United States Patent [19]

Coy et al.

[11] Patent Number: 5,462,926
[45] Date of Patent: Oct. 31, 1995

[54] NEUROMEDIN B RECEPTOR ANTAGONISTS WHICH DEMONSTRATE SELECTIVITY

[75] Inventors: David H. Coy, New Orleans, La.; John E. Taylor, Upton, Mass.

[73] Assignees: Biomeasure, Inc., Milford, Mass.; Administrators of the Tulane Educational Fund, New Orleans, La.

[21] Appl. No.: 78,419

[22] Filed: Jun. 17, 1993

Related U.S. Application Data

[63] Continuation-in-part of Ser. No. 919,537, Jul. 27, 1992, abandoned.

[51] Int. Cl.[6] .................... A61K 38/00; C07K 5/00; C07K 7/00; C07K 17/00
[52] U.S. Cl. ................ 514/16; 530/311; 530/328
[58] Field of Search ...................... 530/311, 328; 514/15, 16, 17

[56] References Cited

U.S. PATENT DOCUMENTS 5,003,011   3/1991   Coy et al. ...................... 530/328

FOREIGN PATENT DOCUMENTS

| 0215171 | 3/1987 | European Pat. Off. . |
| 0298732 | 7/1988 | European Pat. Off. . |
| 0395417 | 2/1990 | European Pat. Off. . |
| 0389180 | 9/1990 | European Pat. Off. . |
| 8904666 | 6/1989 | WIPO . |
| 91/09056 | 12/1990 | WIPO . |

*Primary Examiner*—Jill Warden
*Assistant Examiner*—A. M. Davenport
*Attorney, Agent, or Firm*—Fish & Richardson

[57] ABSTRACT

A method of selectively inhibiting biochemical activity of cells induced by neuromedin B. The method includes the step of contacting cells which contain neuromedin B receptor with a cyclic octapeptide, D-Nal-Cys-Tyr-D-Trp-Lys-Val-Cys-Nal-NH$_2$, or an analog thereof.

24 Claims, 4 Drawing Sheets

NEUROMEDIN B RECEPTOR ANTAGONISTS WHICH DEMONSTRATE SELECTIVITY

STATEMENT AS TO FEDERALLY SPONSORED RESEARCH

This invention was made with some support from the National Institutes of Health (Grant No. CA 45153). Accordingly, the U.S. government has certain rights in the invention.

CROSS REFERENCE TO RELATED APPLICATION

This application is a continuation-in-part of U.S. patent application Ser. No. 07/919,537, filed Jul. 27, 1992, now abandoned.

BACKGROUND OF THE INVENTION

The mammalian bombesin (Bn)-related peptides, gastrin-releasing peptide (GRP) and neuromedin B (NMB) have a wide range of biological and pharmacological effects. These include stimulation of the release of numerous gastrointestinal hormones and peptides, stimulation of exocrine gland secretion chemotaxis, contraction of smooth muscle, effects in the central nervous system such as thermoregulation, behavioral effects, maintenance of circadian rhythm, inhibition of TSH release and satiety. Bn-related peptides also function as a growth factor in numerous normal cells (e.g., bronchial cells, endometrial stomal cells and 3T3 cells) as well as neoplastic cells such as human small cell lung cancer cells, rat hepatocellular tumor cells, prostatic cells and breast adenocarcinoma cells.

Recent structure-function and cloning studies demonstrate that at least two classes of receptors mediate the actions of Bn-related peptides. One class, the GRP-preferring subtype (GRP receptor or GRP-R), has a high affinity for GRP and low affinity for NMB, whereas the other class, the NMB-preferring subtype (NMB receptor or NMB-R), has a high affinity for NMB and lower affinity for GRP. Both classes of receptors are widely present both in the central nervous system and in the gastrointestinal tract. Until recently, the physiological importance of Bn-related peptides in mediating various processes or which receptor subtype mediated the various reported biological effects of Bn-related peptides was unclear.

Five different classes of Bn-receptor antagonists have been described. Jensen, R. T. et al. *Trends Pharmacol. Sci.* 12:13 (1991). Members of a number of these classes have high potency, long duration of action and selectivity for the GRP receptor and thus are useful even in vivo for defining the role of GRP or GRP receptors in mediating various physiological events. However, at present, no antagonists for the NMB receptor which are sufficiently selective or potent have been described. Furthermore, when applied to NMB, none of the methodologies was used successfully to make potent selective GRP receptor antagonists such as synthesizing NMB pseudopeptides or desMet$^9$ NMB or desMet$^9$ NMB esters yields NMB receptor antagonists. Because of the absence of selective antagonists for NMB-R, it has been difficult to evaluate the physiological significance of NMB.

Recently, it was reported that a native somatostatin (SS), somatostatin-14 (SS-14), inhibited the cross-linking of $^{125}$I-GRP to a 120 kD protein in triton extracts of 3T3 cells and human small cell lung cancer cells which are known to possess bombesin receptors. Recent studies have also demonstrated SS-14 could also weakly inhibit binding to opiate receptors, and subsequent structure-function led to the identification of various D-amino acid-substituted and constrained amino acid-substituted cyclo somatostatin analogs that functioned as potent mu opioid receptor antagonists.

SUMMARY OF THE INVENTION

Abbreviations
Nal=3-(2-naphthyl)-alanine or 3-(1-naphthyl)-alanine
Bpa=3-(4-biphenyl)-alanine
X-Phe=phenylalanine with a p-, o- or m-substituent X at its benzene ring, e.g., 3-(4-chlorophenyl)-alanine
F$_5$Phe=3-(pentafluorophenyl)-alanine
Nle=norleucine
Me-Trp=Trp with its indolyl nitrogen substituted with methyl

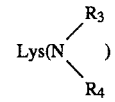

=Lys with its ε amino group substituted with R$_3$ and R$_4$. Thus, Lys(iPr) and Lys(diEt) stand for Lys residues with their ε amino groups monosubstituted by an isopropyl group and disubstituted by two ethyl groups, respectively.

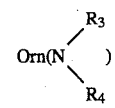

=Orn with its δ amino group substituted with R$_3$ R$_4$

The present invention relates to a method of selectively inhibiting biochemical activity of cells induced by neuromedin B.

One embodiment of the method includes the step of contacting the cells with an octapeptide of the formula:

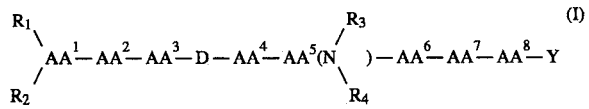

wherein
AA$^1$ is the D- or L-isomer of an aromatic α-amino acid;
AA$^2$ is the D- or L-isomer of Cys;
AA$^3$ is F$_5$Phe, Phe, or X-Phe in which X is halogen, NO$_2$, CH$_3$, or OH;
AA$^4$ is Trp or an aromatic α-amino acid;
AA$^5$ is Lys or Orn;
AA$^6$ is Leu, Ile, Nle, Val, Nal, Trp, Me-Trp, Bpa, F$_5$Phe, Phe, or X-Phe in which X is halogen, NO$_2$, CH$_3$, or OH;
AA$^7$ is the D- or L-isomer of Cys;
AA$^8$ is the D- or L-isomer selected from the group consisting of an aromatic α-amino acid, Thr and Ser;
each R$_1$ and R$_2$, independently, is H, C$_{1-12}$ alkyl, C$_{2-12}$ alkenyl, C$_{2-12}$ alkynyl, phenyl, naphthyl, C$_{7-12}$ phenylalkyl, C$_{8-12}$ phenylalkenyl, C$_{8-12}$ phenylalkynyl, C$_{11-20}$ naphthylalkyl, C$_{12-20}$ naphthylalkenyl, C$_{12-20}$ naphthylalkynyl, COE, or COOE in which E is C$_{1-12}$ alkyl, C$_{2-12}$ alkenyl, C$_{2-12}$ alkynyl, phenyl, naphthyl, C$_{7-12}$ phenylalkyl, C$_{8-12}$ phenylalkenyl, C$_{8-12}$ phenylalkynyl, C$_{11-20}$ naphthylalkyl, C$_{12-20}$ naphthylalkenyl, or C$_{12-20}$ naphthylalkynyl, provided that when one of $R_1$ or $R_2$ is COE or COOE, the other must be H;

each $R_3$ and $R_4$, independently, is H, $C_{1-12}$ alkyl, $C_{2-12}$ alkenyl, $C_{2-12}$ alkynyl, phenyl, naphthyl, $C_{7-12}$ phenylalkyl, $C_{8-12}$ phenylalkenyl, $C_{8-12}$ phenylalkynyl, $C_{11-20}$ naphthylalkyl, $C_{12-20}$ naphthylalkenyl, or $C_{12-20}$ naphthylalkynyl; and Y is $OR_5$ or $NR_6R_7$ in which each $R_5$, $R_6$ and $R_7$, independently, is H, $C_{1-12}$ alkyl, $C_{2-12}$ alkenyl, $C_{2-12}$ alkynyl, phenyl, naphthyl, $C_{7-12}$ phenylalkyl, $C_{8-12}$ phenylalkenyl, $C_{8-12}$ phenylalkynyl, $C_{11-20}$ naphthylalkyl, $C_{12-20}$ naphthylalkenyl, or $C_{12-20}$ naphthylalkynyl; provided that $AA^1$ and $AA^2$ cannot both be D-isomers; and further provided that if $AA^8$ is Thr or Ser, $AA^6$ cannot be Val.

Octapeptides which can be used to practice this embodiment include, but are not limited to:

$H_2$-D-Nal-Cys-Tyr-D-Trp-Lys-Val-Cys-Nal-$NH_2$ (Analog #1);

$H_2$-D-Nal-Cys-Tyr-D-Trp-Lys-Nal-Cys-Thr-$NH_2$ (Analog #2);

$H_2$-D-Nal-Cys-Tyr-D-Trp-Lys-Nal-Cys-Nal-$NH_2$ (Analog #3);

$H_2$-D-Phe-Cys-Tyr-D-Trp-Lys-Val-Cys-Nal-$NH_2$ (Analog #4);

$H_2$-D-Nal-Cys-Tyr-D-Trp-Lys-Val-Cys-D-Nal-$NH_2$ (Analog #8);

$H_2$-Nal-Cys-Tyr-D-Trp-Lys-Val-Cys-D-Nal-$NH_2$ (Analog #9);

$H_2$-D-Nal-D-Cys-Tyr-D-Trp-Lys-Val-Cys-Nal-$NH_2$ (Analog #10);

$H_2$-D-Nal-Cys-Tyr-D-Trp-Lys-Val-D-Cys-Nal-$NH_2$ (Analog #11);

$H_2$-D-Trp-Cys-Tyr-D-Trp-Lys-Val-Cys-Nal-$NH_2$ (Analog #12);

$H_2$-D-Nal-Cys-Tyr-D-Trp-Lys-Phe-Cys-Nal-$NH_2$ (Analog #13);

$H_2$-D-Nal-Cys-Tyr-D-Nal-Lys-Val-Cys-Nal-$NH_2$ (Analog #17);

$H_2$-D-Phe-Cys-Tyr-D-Trp-Lys-Nal-Cys-Thr-$NH_2$; and $H_2$-D-Nal-Cys-Tyr-D-Trp-Orn-Val-Cys-Nal-$NH_2$.

Another embodiment of the present invention relates to a method of selectively inhibiting biochemical activity of cells induced by neuromedin B, the method comprising the step of contacting the cells with an octapeptide of the formula:

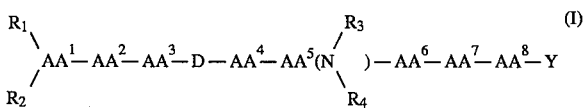 (I)

wherein $AA^1$ is the D- or L-isomer of an aromatic α-amino acid;

$AA^2$ is the D- or L-isomer of Cys;

$AA^3$ is $F_5$Phe, Phe, or X-Phe in which X is halogen, $NO_2$, $CH_3$, or OH;

$AA^4$ is Trp or an aromatic α-amino acid;

$AA^5$ is Lys or Orn;

$AA^6$ is Thr or Ser;

$AA^7$ is the D- or L-isomer of Cys;

$AA^8$ is the D- or L-isomer selected from the group consisting of an aromatic α-amino acid;

each $R_1$ and $R_2$, independently, is H, $C_{1-12}$ alkyl, $C_{2-12}$ alkenyl, $C_{2-12}$ alkynyl, phenyl, naphthyl, $C_{7-12}$ phenylalkyl, $C_{8-12}$ phenylalkenyl, $C_{8-12}$ phenylalkynyl, $C_{11-20}$ naphthylalkyl, $C_{12-20}$ naphthylalkenyl, $C_{12-20}$ naphthylalkynyl, COE, or COOE in which E is $C_{1-12}$ alkyl, $C_{2-12}$ alkenyl, $C_{2-12}$ alkynyl, phenyl, naphthyl, $C_{7-12}$ phenylalkyl, $C_{8-12}$ phenylalkenyl, $C_{8-12}$ phenylalkynyl, $C_{11-20}$ naphthylalkyl, $C_{12-20}$ naphthylalkenyl, or $C_{12-20}$ naphthylalkynyl, provided that when one of $R_1$ or $R_2$ is COE or COOE, the other must be H;

each $R_3$ and $R_4$, independently, is H, $C_{1-12}$ alkyl, $C_{2-12}$ alkenyl, $C_{2-12}$ alkynyl, phenyl, naphthyl, $C_{7-12}$ phenylalkyl, $C_{8-12}$ phenylalkenyl, $C_{8-12}$ phenylalkynyl, $C_{11-20}$ naphthylalkyl, $C_{12-20}$ naphthylalkenyl, or $C_{12-20}$ naphthylalkynyl; and Y is $OR_5$ or $NR_6R_7$ in which each $R_5$, $R_6$ and $R_7$, independently, is H, $C_{1-12}$ alkyl, $C_{2-12}$ alkenyl, $C_{2-12}$ alkynyl, phenyl, naphthyl, $C_{7-12}$ phenylalkyl, $C_{8-12}$ phenylalkenyl, $C_{8-12}$ phenylalkynyl, $C_{11-20}$ naphthylalkyl, $C_{12-20}$ naphthylalkenyl, or $C_{12-20}$ naphthylalkynyl; provided that $AA^1$ and $AA^2$ cannot both be D-isomers.

Octapeptides which can be used to practice this second embodiment include, but are not limited to: $H_2$-D-phe-Cys-Tyr-D-Trp-Lys-Thr-Cys-Nal-$NH_2$ (Analog #7); $H_2$-D-phe-Cys-Tyr-D-Trp-Lys(ipr)-Thr-Cys-Nal-$NH_2$ (Analog #15); $H_2$-D-Phe-Cys-Tyr-D-TrP-Lys(diEt)-Thr-Cys-Nal-$NH_2$ (Analog #16); $H_2$-D-Phe-Cys-Tyr-D-TrP-Lys-Ser-Cys-Thr-$NH_2$; $H_2$-D-Nal-Cys-Tyr-D-Trp-Lys-Thr-Cys-Nal-$NH_2$; $H_2$-D-Nal-D-Cys-Tyr-D-Trp-Lys-Thr-Cys-Nal-$NH_2$; and $H_2$-D-Nal-Cys-Phe-D-Trp-Lys-Thr-Cys-Nal-$NH_2$.

In formula (I), the N-terminus is at the left and the C-terminus at the right in accordance with the conventional representation of a polypeptide chain. The symbol $AA^1$, $AA^2$, or the like in a peptide sequence stands for an amino acid residue, i.e., =N—CH(R)—CO— when it is at the N-terminus or —NH—CH(R)—CO— when it is not at the N-terminus, where R denotes the side chain of that amino acid residue. Thus, R is -CH($CH_3$)$_2$ for Val. Also, when the amino acid residue is optically active, it is the L-form configuration that is intended unless D-form is expressly designated.

Note that the two Cys residues (i.e., $AA^2$ and $AA^7$) in formula (I) are linked together via a disulfide bond. However, for convenience a line which is used conventionally to denote a disulfide bond between two Cys residues is omitted herein. COE stands for

and COOE for

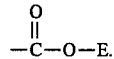

What is meant by "aromatic α-amino acid" is an amino acid residue of the formula

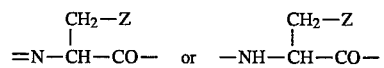

where Z is a moiety containing an aromatic ring. Examples of Z include, but are not limited to, a benzene ring and the following structures with or without a substituent X on the aromatic ring (where X is halogen, $NO_2$, $CH_3$, or OH):

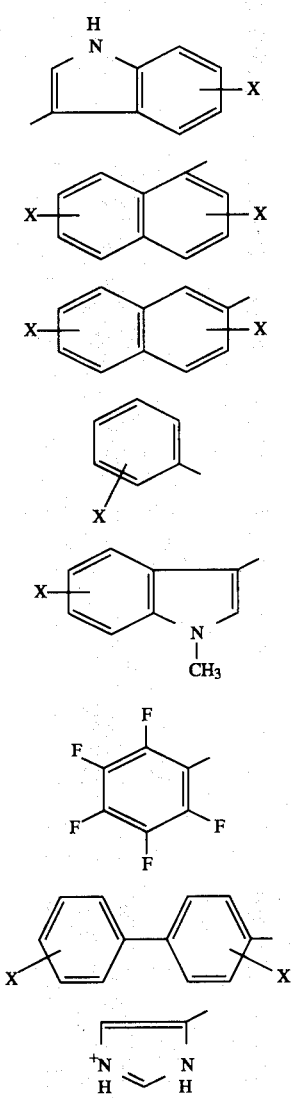

Other examples of an aromatic α-amino acid of the invention are substituted His, such as MeHis, His(τ-Me), or His(π-Me).

Administration of a pharmaceutically acceptable salt of an octapeptide covered by formula (I) into a patient whose disorder arises from biochemical activity induced by NMB is also within the present invention. In other words, the octapeptides can be provided in the form of pharmaceutically acceptable salts, e.g., acid addition salts, or metal complexes, e.g., with zinc, iron or the like. Illustrative examples of acid addition salts are those with organic acids such as acetic, lactic, pamoic, maleic, citric, malic, ascorbic, succinic, benzoic, palmitic, suberic, salicylic, tartric, methanesulfonic or toluenesulfonic acid, those with polymeric acids such as tannic acid or carboxymethyl cellulose, and those with inorganic acids such as hydrochloric acid, hydrobromic acid, sulfuric acid or phosphoric acid.

The term "selectively" as recited in "selectively inhibiting biochemical activity of cells induced by neuromedin B" refers to preferred inhibition of NMB-stimulated production of inositol phosphates over GRP-stimulated amylase release. Such preference of the analogs used to practice the present invention is clearly shown in Table 2 below.

Other features and advantages of the present invention will be apparent from the following drawings and description of the preferred embodiments, and also from the appending claims.

DESCRIPTION OF THE PREFERRED EMBODIMENTS

Figure 1:
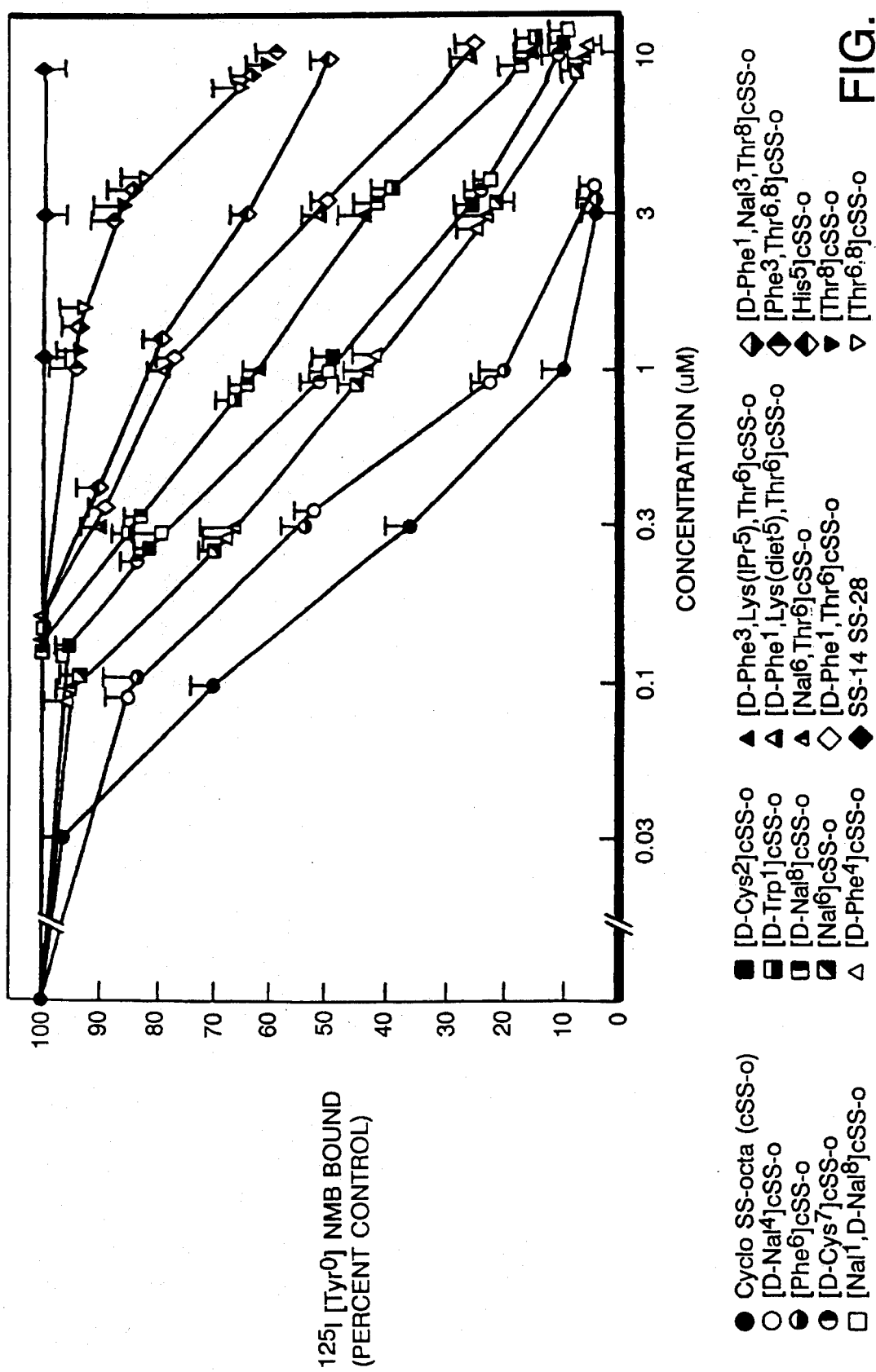
FIG. 1 is a graph showing the ability of various somatostatin octapeptide analogs to inhibit binding of $^{125}$I[D-Tyr$^0$]NMB to NMB receptors on NMB-R transfected cells.

Certain somatostatin octapeptide analogs function as NMB-R receptor antagonists and have>100-fold higher affinity for NMB-R than GRP-R. The most potent analog, cyclo SS-octa or H$_2$-D-Nal-Cys-Tyr-D-Trp-Lys-Val-Cys-Nal-NH$_2$, inhibited binding of $^{125}$I-[D-Tyr$^0$]NMB to NMB receptors on NMB-R transfected 3T3 cells (K$_d$ 216 nM) and on glioblastoma C-6 cells (K$_d$ 59 nM). This analog had a 100-fold lower affinity for GRP-R receptors on rat pancreatic acini.

Structure-function studies performed by synthesizing numerous structurally related SS-octapeptide analogs show that each of these analogs but not native SS-14 or SS-28 also inhibited binding to NMB receptors. [For Structures of SS-14 and SS-28 are well known in the art, see, e.g., Bachem California 1991–1992 Catalog, Torrance, Calif., hereby incorporated by reference.] The stereochemistry at positions 1, 2, 7, and 8, the hydrophobicity and ring size of the substitution in positions 1, 3, and 4 and the basicity of the group in position 5 all were important in determining NMB-R affinity. Each SS-octa analog did not increase [$^3$H]IP in NMB-R transfected cells; however, each inhibited NMB-stimulated increases. The ability of each SS-octa analog to inhibit binding correlated closely with its ability to inhibit NMB-stimulated increases in [$^3$H]IP.

The most potent analog, cyclo SS-octa, caused a parallel rightward shift of the NMB dose-response curve, the Schild plot was not significantly different from unity and the affinity was 230 nM. Furthermore, 0.5 μM cyclo SS-octa caused a decrease in the NMB-R affinity and no change in the number of NMB-R binding sites demonstrating competitive antagonism. Cycle SS-octa did not inhibit Bn-stimulated amylase release from GRP receptor on pancreatic acini or increases in [$^3$H]IP by endothelin in C-6 cells, nor binding of a number of different ligands to non-Bn-related receptors. Structure-function studies demonstrated that the SS-octa analogs also interacted with SS receptors and mu opioid receptors; however, there was no correlation between their affinities for these receptors and NMB-R, demonstrating these activities can be separated. The results demonstrate for the first time a class of antagonists with >100-fold selectivity for NMB than GRP receptors.

It is believed that one skilled in the art can, based on the description herein, utilize the present invention to its fullest extent. The following specific embodiments are, therefore, to be construed as merely illustrative, and not limitative of the remainder of the disclosure in any way whatsoever. All of the documents cited below are hereby incorporated by reference.

EXPERIMENTAL INFORMATION

MATERIALS:

Rat glioblastoma C-6 cells were obtained from the American Type Culture Collection (Rockville, Md.), Dulbecco's modified essential medium, fetal bovine serum, and Geneticin (aminoglycoside G-418) were from GIBCO (Waltham, Mass.), and cell culture flasks and 24-well plates were obtained from Costar Co. (Cambridge, Mass.).

Bovine serum albumin (fraction V) and HEPES were obtained from Boehringer Mannheim Biochemicals (Indianapolis, Ind.); soybean trypsin inhibitor, EGTA, and bacitracin were from Sigma Chemical Co. (St. Louis, Mo.); glutamine was from the Media Section, National Institutes of Health (Bethesda, Md.); NMB, [Tyr$^4$]Bn, bombesin, GRP, and endothelin 1 (ET-1) were from Peninsula Laboratories (Belmont, Calif.); Na$^{125}$I was from Amersham Co. (Arlington Heights, Ill.); myo-[2-$^3$H]inositol (16–20 Ci/mmol) was from New England Nuclear (Boston, Mass.); somatostatin-14 (SS-14) and somatostatin-28 (SS-28) were from Bachem (Torrence, Calif.); Dowex AG 1-X8 anion exchange resin (100–200 mesh, formate form) was from Bio-Rad (Richmond, Calif.); Hydro-Fluor scintillation fluid, methanol (absolute), and hydrochloric acid were from the J. T. Baker Chemical Co. (Phillipsburg, N.J.).

METHODS:

Transfection and maintenance of cell lines

As described previously [Wada, E., et al. *Neuron* 6:421 (1991)], BALB 3T3 cells expressing a stably transfected rat NMB receptor (NMB-R transfected cells) were obtained using calcium phosphate precipitation of a full length NMB-preferring bombesin receptor clone generated from rat esophagus and subcloned into a modified version of the pCD2 plasmid. Cells were passaged every 3–4 days at confluence, using 0.1% trypsin in 1 mM EDTA. Rat glioblastoma C-6 tumor cells were maintained similarly and were passaged weekly at confluence. Both cell lines were cultured at 37° C. in a 5% CO$_2$ atmosphere. Rat AR 42J pancreatic acinar cells were cultured in Dulbecco's modified Eagle's medium (DMEM) without antibiotics and supplemented with 10% (vol/vol) fetal calf serum. The incubation atmosphere consisted of 10% CO$_2$-90% humidified air at 37° C.

Preparation of rat pancreatic acini

Dispersed acini from guinea pig pancreas were prepared as described previously [Jensen, R. T. et al. *J. Biol. Chem.* 257:5554 (1982); and Peikin, S. R. et al. *Am. J. Physiol.* 235:G743 (1978)].

Preparation of peptides

Peptides were synthesized on methybenzhydrylamine resin using standard solid phase procedures and cleaved with hydrogen fluoride/anisol mixtures. Peptides were cyclized in dilute 90% acetic acid solution by titration with I$_2$ and purified by gel filtration on Sephadex G-25 in 50% acetic acid and gradient elution on C18 silica using acetonitrile/ 0.1% trifluoroacetic acid buffers. The methods have been described in detail previously [Sasaki, Y. et al. *J. Med. Chem.* 30:1162 (1987); Stewart, J. M. et al. Solid Phase Peptide Synthesis, 2nd Ed., Pierce Chemical Co., Rockford, Ill. (1984); and Coy, D. H. et al. *Tetrahedron*, 44:835 (1988), all of which are incorporated herein by reference.]. Homogeneity was assessed by thin layer chromatography, analytical HPLC, amino acid analysis and mass spectrometry and was determined to be >96% for each peptide.

Below is a detailed description regarding the synthesis of Analog #1. Other peptides of the invention can be prepared by making appropriate modifications, within the ability of someone of ordinary skill in this field, of the synthetic methods disclosed herein.

Step 1: Preparation of Boc-D-Nal-S-methylbenzyl-Cys-O-bromobenzyloxycarbonyl-Tyr-D-Trp-N-benzyloxycarbonyl-Lys-Val-S-methylbenzyl-Cys-Nal-benzhydrylamine resin Benzhydrylamine-polystyrene resin (Advanced Chem Tech, Inc.) (1.2 g, 0.5 mmole) in the chloride ion form was placed in the reaction vessel of an Advanced Chem Tech peptide synthesizer programmed to perform the following reaction cycle: (a) methylene chloride; (b) 33% trifluoroacetic acid in methylene chloride (2 time for 1 and 25 min each); (c) methylene chloride; (d) ethanol; (e) methylene chloride; (f) 10% triethylamine in chloroform.

The neutralized resin was stirred with t-butyloxycarbonyl("Boc")-Nal and diisopropylcarbodiimide (1.5 mmole each) in methylene chloride for 1 hr and the resulting amino acid resin was then cycled through steps (a) to (g) in the above wash program. The following amino acids (1.5 mmole) were then coupled successively by the same procedure: Boc-S-methylbenzyl-Cys, Val, Boc-N-benzyloxycarbonyl-Lys, Boc-D-Trp, Boc-O-bromobenzyloxycarbonyl-Tyr, and Boc-S-methylbenzyl-Cys and Boc-D-Nal. After washing and drying, the completed resin weighed 1.78 g.

Step 2: Preparation of H-D-Nal-Cys-Tyr-D-Trp-Lys-Val-Cys-Nal-NH$_2$

The peptide resin obtained from Step 1 (1.78 g, 0.5 mmole) was mixed with anisole (5 ml), dithiothreitol (100 mg) and anhydrous hydrogen fluoride (35 ml) at 0° C. and stirred for 45 min. Excess hydrogen fluoride was evaporated rapidly under a stream of dry nitrogen and free peptide precipitated and washed with ether. The crude peptide was then dissolved in 500 ml of 90% acetic acid to which was added a concentrated solution of I$_2$/MeOH until a permanent brown color was observed. Excess I$_2$ was removed by addition of ascorbic acid and the solution evaporated to a small volume which was applied to a column (2.5×90 cm) of Sephadex G-25 which was eluted with 50% AcOH. Fractions containing a major component by UV absorption and thin layer chromatography ("TLC") were then pooled, evaporated to a small volume and applied to a column (1.5×70 cm) of Vydac octadecylsilane silica (10–15 µ), followed by elution with a linear gradient of acetonitrile in 0.1% trifluoroacetic acid in water. Fractions were examined by TLC and analytical high performance liquid chromatography ("HPLC") and pooled to give maximum purity.

Repeated lyophilization of the solution from water gave 151 mg of the product as a white, fluffy powder. The product was found to be homogeneous by HPLC and TLC. Amino acid analysis of an acid hydrolysate and FAB MS confirmed the composition of the octapeptide.

Preparation of $^{125}$I-[D-Tyr$^0$]NMB $^{125}$I-[D-Tyr$^0$]NMB (2200 Ci/mmol) was prepared using Iodo-Gen as described recently [Benya, R. V. et al. *Mol. Pharmacol.* 42:1058 (1992)]. In brief, 0.4 µg of Iodo-Gen was added to 8.0 µg of [D-Tyr$^0$]NMB with 2 mCi of Na$^{125}$I in 20 µl of 0.5M KH$_2$PO$_4$ buffer (pH 7.4). After incubation at 22° C. for 6 min, 300 μl of 1.5M dithiothreitol were added and the reaction mixture was incubated at 80° C. for 60 min. Free $^{125}$I was separated by applying the reaction mixture to a Sep-Pak cartridge (Waters Associates, Milford, Mass.), which had been prepared by washing with 5 ml of methanol, 5 ml of 0.1% trifluoroacetic acid, and 5 ml of water. Free $^{125}$I was eluted with 200-μl sequential elutions (10 times) of 60% acetonitrile/0.1% trifluoroacetic acid. Radiolabeled peptide was separated from unlabeled peptide by combining the three elutions with the highest radioactivity and applying them to a reverse phase high performance liquid chromatograph (Waters Associates model 204, with a Rheodyne injector), using a 0.46-×25-cm μBondaPak column. The column was eluted with a linear gradient of acetonitrile and 0.1% trifluoroacetic acid (v/v) from 16 to 64% acetonitrile in 60 min, with a flow rate of 1.0 ml/min. $^{125}$I-[D-Tyr$^0$]NMB was stored with 1% (w/v) BSA at −20° C. and was stable for at least 6 weeks.

Binding of $^{125}$I-[D-Tyr$^0$]NMB to C-6 glioblastoma and NMB-R transfected cells Binding studies using rat glioblastoma C-6 or NMB-R transfected cells were performed as described previously [Benya, R. V. et al. *Mol. Pharmacol.* 42:1058 (1992); and Wang, L-H. et al. *Biochem. J.* 286:641 (1992)] by suspending disaggregated cells in binding buffer, which was composed of standing buffer (130 nM NaCl, 7.7 mM KCl, 1.0 mM EGTA, 0.02% soybean trypsin inhibitor) additionally containing 50 mM HEPES, 1 mM MgCl$_2$, 1.5 mM CaCl$_2$, 2.2 mM KH$_2$PO$_4$, 0.015% glutamine, and 0.2% BSA (w/v) (pH 7.4). Incubations contained 75 pM $^{125}$I-[D-Tyr$^0$]NMB and 15×10$^6$ C-6 cells/ml or 2×10$^6$ NMB-R transfected cells/ml, for 60 min at 22° C. Nonsaturable binding of $^{125}$I-[D-Tyr$^0$]NMB was the amount of radioactivity associated with C-6 cells or NMB-R transfected cells when the incubation mixture contained in μM NMB. Nonsaturable binding was<15% of total binding in all experiments; all values are reported herein as saturable binding (i.e., total minus nonsaturable binding).

Binding of $^{125}$I-labeled [Tyr$^4$]bombesin to acini. $^{125}$I-[Tyr$^4$]bombesin (2000 Ci/mmol) was prepared using the modification [Von Screnck et al. *Am. J. Physiol.* 256:G747 (1989)] of the method as described previously [Jensen, R. T. et al. *Proc. Natl. Acad. Sci. USA* 75:6139 (1978)]. $^{125}$I-[Tyr$^4$]bombesin was separated from $^{125}$I using a Sep-Pak cartridge and separated from unlabeled peptide by reverse-phase high pressure liquid chromatography on a column (0.46×25 cm) of μBondapak C$_{18}$. The column was eluted isocratically with acetonitrile (22.5%) and triethylammonium phosphate (0.25M, pH 3.5) (77.5%) at a flow rate of 1 ml/min. Incubations contained 50 pM $^{125}$I-[Tyr$^4$]bombesin and were for 60 min at 37° C. with pancreatic acini. Nonsaturable binding of $^{125}$I-[Tyr$^4$]bombesin was the amount of radioactivity associated with the acini when the incubate contained 50 pM $^{125}$I-[Tyr$^4$]bombesin plus 1 μM bombesin. All values shown are for saturable binding, i.e., binding measured with $^{125}$I-[Tyr$^4$]bombesin alone (total) minus binding measured in the presence of 1 μM unlabeled bombesin (nonsaturable binding). Nonsaturable binding was<10% of total binding in all experiments.

Membrane receptor assays

Membranes were prepared from rat olfactory bulb (NMB membrane receptor assay), AR 42J cells (GRP and somatostatin membrane receptor assays), guinea pig cerebral (N$_1$, histamine H$_1$, and sigma opioid membrane receptor assays), rat pancreas (CCK$_A$ receptor assay), rat cerebral cortex (CCK$_B$, PYY, neurotensin, α$_1$-adrenergic, α$_2$-adrenergic, muscarinic cholinergic, neural benzodiazepine, peripheral benzodiazepine, adenosine, calcium channel, and N-methyl-D-asparate membrane receptor assays), A$_{10}$ smooth muscle cells (Et$_A$ membrane receptor assay), rat forebrain (TRH, mu and delta opioid membrane assays), rat corpus striatum (dopamine$_1$ and dopamine$_2$ membrane receptor assays), and rat frontal cortex (serotonin$_2$ membrane receptor assay). Membranes were prepared using a Polytron (setting 6, 15 sec) in ice-cold 50 mM Tris-HCl unless otherwise specified below and centrifuged twice at 39,000× g/10 min) with an intermediate resuspension in fresh buffer. For the NMB and GRP membrane receptor assay, final pellets were resuspended in 50 mM Tris-HCl containing 0.1 mg/ml bacitracin, and 0.1% BSA and for the somatostatin receptor assay in 10 mM Tris-HCl. For the NMB and GRP membrane binding assay 50 pM $^{125}$I-NMB (or 50 pM $^{125}$I-[Tyr$^4$]Bn) was used with a 30 min incubation at 4° C., whereas for the somatostatin assay the incubation was 25 min at 30° C. with 50 pM $^{125}$I-[Tyr$^1$]somatostatin in 50 mM HEPES (pH 7.4) with 0.1% BSA, 5 mM MgCl2, bacitracin (0.02 mg/ml), trasylol (200 KIU/ml) and phenylmethylsulfonyl fluoride (PMSF) (0.02 mg/ml). Incubations were terminated by rapid filtration through GF/B filters presoaked in 0.1% polyethyleneimine (NMB and GRP receptor assays). Each filter was washed three times with 5 ml aliquots of ice-cold buffer. The ligands used for the various membrane binding assays were [$^3$H]substance P (NK$_1$ receptor), [$^{125}$I]endothelin-1 (endothelin$_A$ receptor), [$^{125}$I]CCK-8 (CCK$_A$ and CCK$_B$ receptors), [$^{125}$I]PYY (PYY receptor), [$^3$H]neurotensin (neurotensin receptor), [$^3$H]bradykinin (bradykinin$_2$ receptor), [$^3$H]3-meHisTRH (TRH receptor), [$^3$H]prazosin (ω$_1$ adrenergic receptor), [$^3$H]clonidine (ω$_2$ adrenergic receptor), [$^3$H]dihydroalprenolol (β$_1$ adrenergic receptor), [$^3$H]QNB (muscarinic cholinergic receptor), [$^3$H]RO15-1788 (benzodiazepine-neural receptor), [$^3$H]RO5-4864 (benzodiazepine-peripheral receptor), [$^3$H]SCh 23390 (dopamine$_1$ receptor), [$^3$H]spiperone (dopamine$_2$ receptor), [$^3$H]ketanserin (serotonin$_2$ receptor), [$^3$H]pyrilamine (histamine H$_1$ receptor), [$^3$H]cyclohexyladenosine (adenosine$_1$ receptor), [$^3$H]MK-801 (N-methyl-D-aspartate receptor), [$^3$H]pentazocine (sigma opioid receptor), [$^3$H]DAGO (mu opioid receptor) and [$^3$H]DPDPE (dela opioid receptor).

Measurement of phosphoinositides

Total phosphoinositides in C-6 cells and in NMB-R transfected cells were determined as described previously, with minor modifications [Benya, R. V. et al. *Mol. Pharmacol.* 42:1058 (1992); and Wang, L-H. et al. *Biochem. Jo* 286:641 (1992)]. Cells were grown to confluence in 24-well plates and then loaded with 100 μCi/ml myo-[2-$^3$H]inositol in Dulbecco's modified essential medium with 2% fetal bovine serum at 37° C. for 48 hrs. Cells were washed and incubated in phosphoinositide buffer (standard buffer additionally containing 10 mM LiCl, 20 mM HEPES, 2 mM CaCl$_2$, 2% BSA, and 1.2 mM MgSO$_4$) for 15 min and then for 60 min at 37° C. with agonists at various concentrations or with 3 nM NMB (a half-maximal effective concentration) and possible antagonists at different concentrations. Reactions were halted using ice-cold 1% HCl in methanol, and the inositol phosphates (IP) were isolated as described previously [Bologna, M. et al. *Cancer* 63:1714 (1989); and Endo, T. et al. *J. Endocrinolo* 131:313 (1991)]. Briefly, after loading of the anion exchange column, free [$^3$H]glycerophosphorylinositol was removed by washing with 5 mM disodium tetraborate in 60 mM sodium formate. Total [$^3$H] inositol phosphates were then eluted using 100 mM formic acid in 1.0M ammonium formate as described previously [Benya, R. V. et al. *Mol. Pharmacol.* 42:1058 (1992); and Wang, L-H. et al. *Biochem. J.* 286:641 (1992)].

RESULTS:

To investigate the ability of SS-14, SS-28 and the various cycle SS-octa analogs to interact with NMB and GRP receptors, the ability of each to inhibit binding of either $^{125}$I-[D-Tyr$^0$]NMB to NMB-R transfected cells (FIG. 1) or $^{125}$I-[D-Tyr$^4$]Bn to GRP receptors on rat pancreatic acini was determined. At 10 μM, SS-14 and SS-28 caused no inhibition of binding of $^{125}$I-[Tyr$^0$]NMB to NMB-R transfected cells; however, each of the cyclo SS-octapeptide analogs caused significant inhibition of binding of $^{125}$I-[Tyr$^0$]NMB to these cells (FIG. 1). Cyclo SS-octa (#1; Table 1) was the most potent causing detectible inhibition of binding of $^{125}$I-[Tyr$^0$]NMB at 0.1 μM, half-maximal inhibition at 216 nM and complete inhibition at 3 μM (FIG. 1; Table 1). Cyclo SS-octa was 2-fold more potent than [Phe$^6$]-cycle SS-octa (#13; Table 1); and [D-Nal$^4$]-cycle SS-octa (#17; Table 1) (K$_1$ 400 nM; Table 1) which were equipotent; 4-fold more potent than [Nal$^6$, Thr$^8$]-, [Nal$^6$]- and [D-Phe$^1$]-cyclo SS-octa (FIG. 1) (#2–4; Table 1; K$_1$ 700–800 nM); 6-fold more potent than [Nal$^1$, D-Nal$^8$]-cyclo SS-octa, [D-Cys$^2$]- and [D-Cys$^7$]-cyclo SS-octa (FIG. 1) (#9–11; Table 1; K$_1$ 1–1.2 μM); 9-fold more potent than [D-Nal$^8$]-, [D-Trp$^1$]- and [D-Phe$^1$, Lys(iPr)$^{5,}$Thr$^6$]-cyclo SS-octa (#8, 12 and 15; Table 1; K$_1$ 1.4–2.3 μM); 18-fold more potent than [D-Phe$^1$, Lys (diEt)$^5$, Thr$^6$]cyclo SS-octa (#7 and 16; Table 1; K$_1$ 3.9–4.4 μM); 45-fold more potent than [His$^5$]-cyclo SS-octa (#14; Table 1; K$_1$ 9.9 μM) and 69-fold more potent than [Thr$^8$]-, [Thr$^{6,8}$]-, [Phe$^3$,Thr$^{6,8}$]-, and [D-Phe$^1$, Nal$^3$,Thr$^8$]-cycle SS-octa (#5, 6, 18 and 19; Table 1; K$_1$ 14–19 μM). In contrast but similar to SS-14 and SS-28, 13 of the cyclo SS-octapeptides caused no inhibition of $^{125}$I-[Tyr$^4$]Bn binding to GRP receptors on rat pancreatic acini, and the remaining six analogs had very low affinity for this receptor with each having an affinity>15 μM (Table 1). The three most potent analogs, cyclo SS-octa, [Phe$^6$]-cycle SS-octa and [D-Nal$^4$]-cyclo SS-octa (#1, 13 and 17; Table 1) had 84,>100 and>100-fold greater affinity for the NMB than the GRP receptors (Table 1).

TABLE 1

Affinity of SS-14, SS-28 or various ss-octapeptide analogs for NMB receptors on C-6 cells or transfected BALB 3T3 cells or GRP receptors on rat pancreatic acini.

| | NMB Receptor | | | GRP Receptor | |
|---|---|---|---|---|---|
| | C-6 Cells | Transfected Cells | | Rat Pancreatic Acini | |
| Analog # | Ki(nM) $^{125}$I-NMB Binding | IC$_{50}$ (nM) NMB-stimulated [$^3$H]IP | Ki(nM) $^{125}$I-NMB Binding | IC$_{50}$ (nM) Amylase Release | Ki (nM) $^{125}$I-[Tyr$^4$] Bn Binding |
| 1 | 59 ± 9 | 895 ± 98 | 216 ± 36 | — | 18264 ± 2110 |
| 2 | 226 ± 36 | 6673 ± 435 | 772 ± 94 | — | 16291 ± 3818 |
| 3 | 997 ± 76 | 2880 ± 188 | 697 ± 64 | — | — |
| 4 | 848 ± 191 | 3757 ± 568 | 818 ± 68 | — | 21947 ± 4265 |
| 5 | 3792 ± 1084 | — | 14766 ± 2651 | — | — |
| 6 | 8286 ± 2427 | — | 16398 ± 4455 | — | — |
| 7 | 1452 ± 78 | 36235 ± 4974 | 4362 ± 328 | — | 30981 ± 4653 |
| 8 | 670 ± 73 | 5187 ± 987 | 1924 ± 201 | — | — |
| 9 | 1159 ± 214 | 4413 ± 451 | 1156 ± 229 | — | — |
| 10 | 1147 ± 518 | 3992 ± 781 | 960 ± 109 | — | — |
| 11 | 1740 ± 345 | 1427 ± 119 | 1077 ± 199 | — | — |
| 12 | 1778 ± 109 | 4688 ± 927 | 1411 ± 127 | — | — |
| 13 | 213 ± 13 | 1173 ± 114 | 397 ± 72 | — | — |
| 14 | 4944 ± 930 | 11865 ± 1835 | 9863 ± 1294 | — | — |
| 15 | 1142 ± 105 | 9897 ± 2312 | 2328 ± 397 | — | 38127 ± 21549 |
| 16 | 1089 ± 38 | 7212 ± 2795 | 3951 ± 509 | — | — |
| 17 | 313 ± 33 | 1779 ± 295 | 399 ± 68 | — | — |
| 18 | 8322 ± 957 | >10 μM | 19816 ± 4235 | — | 61637 ± 21512 |
| 19 | 8485 ± 1165 | >10 μM | 14341 ± 1819 | — | — |
| SS-14 | — | — | — | — | — |
| SS-15 | — | — | — | — | — |

— = no agonist or antagonist activity at concentrations up to 10 μM. IC$_{50}$ = concentration causing half-maximal inhibition of the indicated agonist. Ki = affinity of the indicated peptide for the indicated receptor calculated by the method of Cheng, Y. C. et al. Biochem. Pharmacol. 22:2099 (1973).

To determine whether SS-14, SS-28 or the various cyclo SS-octapeptide analogs functioned as agonists or antagonists at the Bn receptor subtypes, their ability at 10 μM to stimulate increases in [$^3$H]IP in NMB-R transfected cells or stimulate amylase release or inhibit Bn-stimulated amylase release from rat pancreatic acini possessing GRP receptors was assessed (Table 2). Neither SS-14, SS-28 nor any of the 19 SS-octapeptide analogs at a concentration of 10 μM had agonist activity and stimulated increases in [$^3$H]IP in NMB-R transfected cells or amylase release from rat pancreatic acini which have GRP receptors (Table 2). Similarly, none of these peptides at this concentration altered the increase in amylase release caused by 0.3 nM Bn in rat pancreatic acini (Table 2). Whereas SS-14, SS-28 and 3 cyclo SS-octapeptide analogs (#5, 6 and 18; Table 2) had no effect on the 14-fold increase in [$^3$H]IP caused by 3 nM NMB in NMB-R transfected cells, 16 of the cyclo SS-octapeptide analogs caused some inhibition (Table 2). Five analogs at 10 μM (#1, 10, 11, 13 and 17; Table 2) completely inhibited the NMB-stimulated increase in [$^3$H]IP.

TABLE 2

Affinity of SS-14, SS-28 and related octapeptide analogs to alter NMB-stimulated increases and [³H]IP in NMB-R transfected cells or amylase release in rat pancreatic acini.

| Analog # | NMB-R Transfected Cells [³H]IP (dym × 10³) | | Rat Pancreatic Acini Amylase Release (% total) | |
|---|---|---|---|---|
| | Alone (10 μM) | Plus NMB (3 nM) | Alone (10 μM) | Plus Bn (0.3 nM) |
| | 13 ± 3 | 186 ± 58 | 4 ± 1 | 15 ± 1 |
| 1 | 12 ± 2 | 8 ± 4* | 5 ± 1 | 15 ± 2 |
| 2 | 11 ± 2 | 39 ± 7* | 5 ± 1 | 13 ± 1 |
| 3 | 11 ± 1 | 65 ± 15* | 3 ± 1 | 15 ± 1 |
| 4 | 13 ± 1 | 33 ± 4* | 4 ± 2 | 14 ± 1 |
| 5 | 11 ± 2 | 179 ± 13 | 3 ± 1 | 12 ± 1 |
| 6 | 11 ± 2 | 188 ± 30 | 3 ± 1 | 14 ± 2 |
| 7 | 15 ± 1 | 99 ± 24* | 3 ± 1 | 16 ± 1 |
| 8 | 10 ± 3 | 67 ± 13* | 2 ± 1 | 14 ± 1 |
| 9 | 8 ± 2 | 28 ± 6* | 3 ± 1 | 16 ± 1 |
| 10 | 10 ± 3 | 4 ± 2* | 3 ± 1 | 16 ± 1 |
| 11 | 10 ± 1 | 7 ± 4* | 2 ± 1 | 14 ± 1 |
| 12 | 9 ± 2 | 43 ± 2 | 3 ± 1 | 13 ± 1 |
| 13 | 10 ± 1 | 9 ± 4* | 3 ± 1 | 14 ± 1 |
| 14 | 8 ± 1 | 97 ± 7* | 2 ± 1 | 13 ± 1 |
| 15 | 11 ± 1 | 67 ± 7* | 4 ± 2 | 13 ± 2 |
| 16 | 11 ± 2 | 73 ± 15* | 5 ± 1 | 12 ± 1 |
| 17 | 12 ± 4 | 15 ± 2* | 4 ± 2 | 19 ± 1 |
| 18 | 11 ± 1 | 143 ± 11 | 3 ± 1 | 14 ± 1 |
| 19 | 10 ± 1 | 119 ± 4 | 3 ± 1 | 14 ± 2 |
| SS-14 | 14 ± 1 | 182 ± 24 | 3 ± 1 | 12 ± 1 |
| SS-28 | 12 ± 1 | 177 ± 13 | 4 ± 1 | 10 ± 1 |

Figure 2:
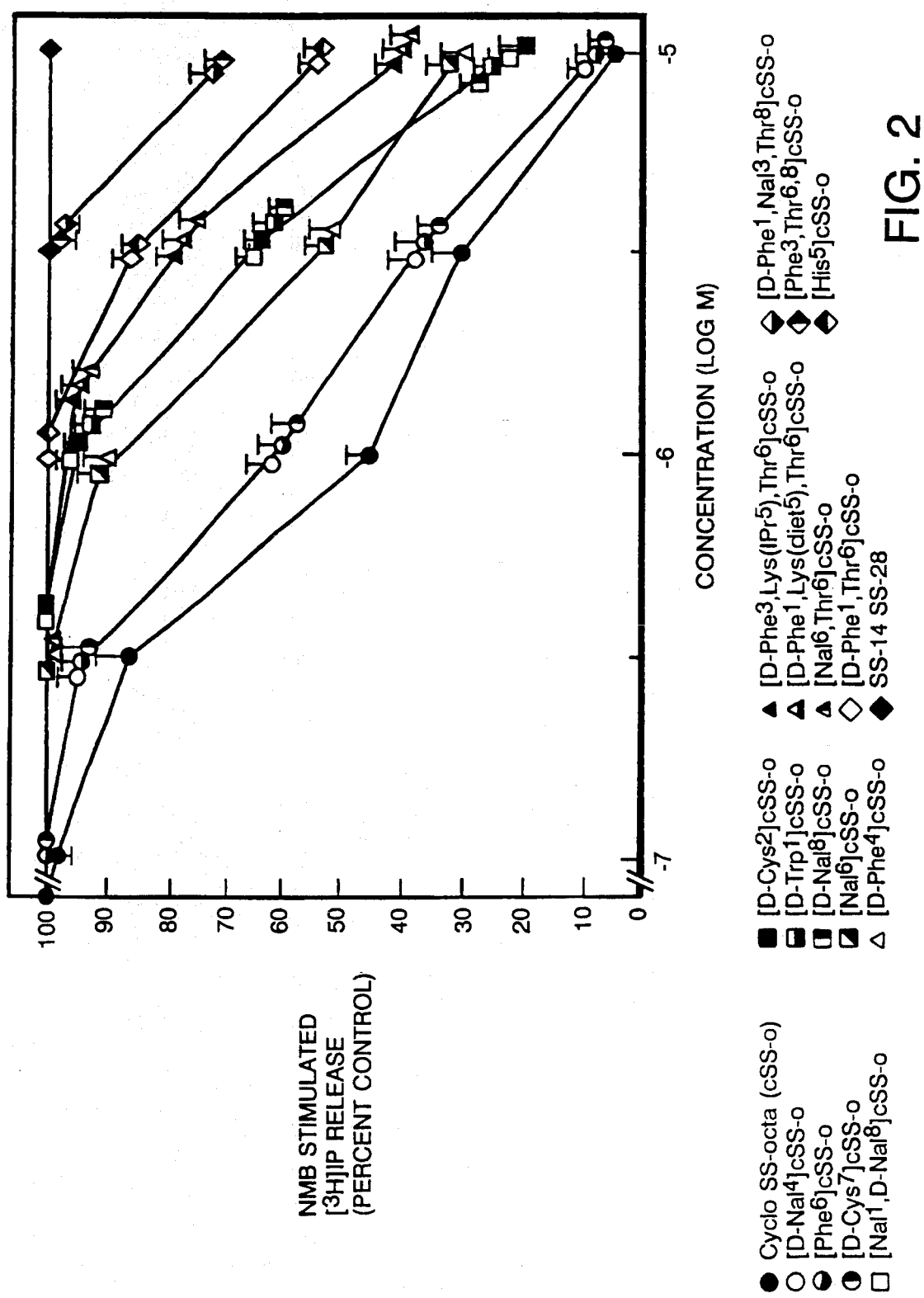
FIG. 2 is a graph showing the ability of SS-14, SS-28 and various cyclo somatostatin octapeptide analogs to inhibit NMB-stimulated increases in [$^3$H]inositol phosphates (IP) in NMB transfected cells.

\* = p <0.05 compared to value with no somatostatin analog added. Rat pancreatic acini or [³H]myo-[2-H]inositol-loaded NMB-R transfected cells were incubated either with no additives, the somatostatin octapeptide analog, Bn, or NMB, or a combination for 30 min at 37° C.. Amylase release from pancreatic acini was expressed at the indicated percent of the total cellular amylase released during the incubation. [³H]IP is expressed in dpm's. To test for inhibitory effects, the effect of somatostatin analog (10 μM) was determined on 0.3 nM Bn-stimulated amylase release or a 4 nM NMB-stimulated increase in [³H]IP which are each half-maximally effective agonist concentrations. Results are means ± ISEM from at least 4 separate experiments and in each experiment, each value was determin To determine the relative abilities of the SS-octapeptide analogs to inhibit NMB-stimulated increases in [³H]IP in NMB-R trans, transfected cells, dose-inhibition curves were determined for each analog (FIG. 2). Cyclo SS-octa (#1; Table 1) was the most potent, causing detectible inhibition at 0.3 μM, half-maximal inhibition at 885 μM and complete inhibition at 10 nM (FIG. 2). The relative potencies were: cyclo SS-octa (#1, IC$_{50}$ 885 nM)>[D-Cys⁷]-, [Phe⁶]-, [D-Nal⁴]-cyclo SS-octa (#11, 13 and 17; Table 1); IC$_{50}$ 1.2–1.8 μM)>[Nal⁶,Thr⁸]-, [Nal⁶]-, [D-Phe¹]-cyclo SS-octa (#2–4; Table 1); IC$_{50}$ 3–6.6 μM)>[D-Nal⁸], [Nal¹,D-Nal⁸]-, [D-Cys²]-, [D-Trp¹]-cyclo SS-octa (#8–10, 12; Table 1; IC$_{50}$ 4.4–5.2 μM)>[D-Phe¹,Lys(iPr)⁵,Thr⁶]-, [D-Phe¹, Lys(diEt)⁵, [Thr⁶]-cyclo SS-octa (#15 and 16; Table 1; IC$_{50}$ 7.2–9.8 μM)>[His⁵]-cyclo-SS-octa (#14; Table 1, IC$_{50}$ 11.8 μM)> [D-Phe¹, Thr⁶]-, [D-Phe¹,Nal³,Thr⁸]-, [Phe³,Thr⁶,⁸]-cyclo-SS-octa (#7, 18 and 19; Table 1, IC$_{50}$>10 μM)>SS-14, SS-28, [Thr⁸]-, [Thr⁶,⁸]-cyclo-SS-octa (#5 and 6, no activity at 10 μM). In general, there was a close agreement between the relative abilities of the different SS-octapeptide analogs to occupy the NMB-receptor and inhibit binding of ¹²⁵I-[D-Tyr⁰]NMB to NMB-R transfected cells and their abilities to inhibit NMB-stimulated increases in [³H]IP in these cells (FIGS. 1, 2; Table 1).

The 18 cyclo SS-octapeptide analogs of cyclo SS-octa were made to explore the importance of the different amino acid substitutions in cyclo SS-octa (#1; Tables 1,2) in determining its ability to function as a NMB receptor antagonist. Analogs 8–11 (Tables 1, 2) explored the importance of stereochemistry at positions 1, 2, 7, 8 of cyclo SS-octa. Changing Cys¹ or Cys⁷ to a D-Cys had an equal effect in decreasing affinity 5-fold for both substitutions (compare #1, 10 and 11; Table 1). Similarly, insertion of a D-Nal in position 8 caused a 6-fold decrease in affinity (compare #1 and 8; Table 1) and the further addition of Nal¹ for D-Nal¹ did not change affinity further (compare #1, 8 and 9; Table 1). The importance of the hydrophobicity and ring size of the substituted amino acid was explored for position 1 (analog #4 and 12; Table 1), position 3 (#18 and 19; Table 1) and position 4 (#17; Table 1). The insertion of a less hydrophobic group with a different ring size, D-Phe¹ or D-Trp¹, had only a moderate effect, decreasing potency 4 to 7-fold (compare #1, 4 and 12; Table 1). In contrast, the insertion of more hydrophobic groups Nal³, D-Phe³ for Tyr³ had almost no effect on affinity (compare #5 and 6 with #18 and 19; Table 1) in that when added to an analog with a Thr⁸ replacement (#5; Table 1) no change in affinity occurred. Similarly, the insertion of the more hydrophobic group D-Nal for D-Trp in position 4 (compare #1 and 17; Table 1) had almost no effect on affinity. The importance of the Val substitution in position 6 of cyclo SS-octa was examined in analogs (#3 and 13; Table 1). Substitution of either Phe⁶ (#13; Table 1) or Nal⁶ (#3; Table 1) caused only a minimal (2 to 3-fold) decrease in affinity. The insertion of Thr⁸ in position similar to that used in some high affinity SS or mu receptor agonists [Maurer, R. et al. Proc. Natl. Acad. Sci. USA 79:4815 (1982); Pelton, J. T. et al. Proc. Natl. Acad. Sci. 82:236 (1985); Gulya, K., et al. Life Sci. 38:2225 (1986); and Walker, J. M. et al. Peptides 8:869 (1987)], caused a dramatic (80-fold) decrease in NMB receptor affinity (compare #1 and 5; Table 1), whereas insertion of a Nal for Val⁶ compensated for the Thr⁸ substitution and resulted in only a 4-fold decrease (compare #1, 2 and 5; Table 1). The substitution of a less basic group His$^5$ in position 5 for Lys caused a marked 50-fold decrease in affinity (compare #1 and 14; Table 1). Altering the availability of the primary amino group on Lys$^3$ by formation of diethyl Lys$^3$ or isopropyl Lys$^3$ caused little change in affinity for the NMB receptor (compare #7, 15 and 6; Table 1).

Figure 3:
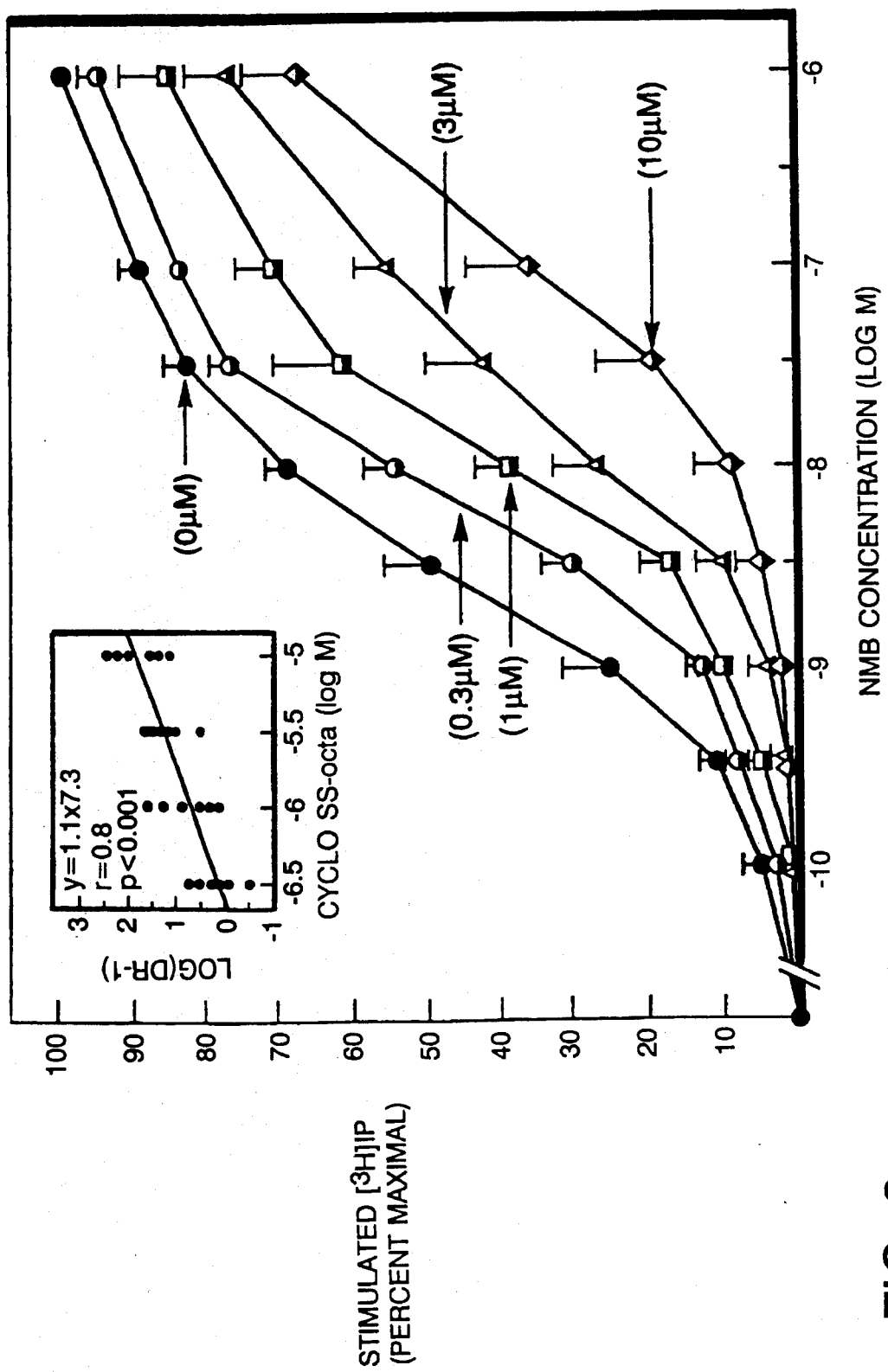
FIG. 3 is a graph showing the effect of increasing concentrations of cyclo SS-octa (i.e., Analog #1) on the dose-response curve for NMB-stimulated increases in [$^3$H]IP in NMB-R transfected cells.
Figure 4:
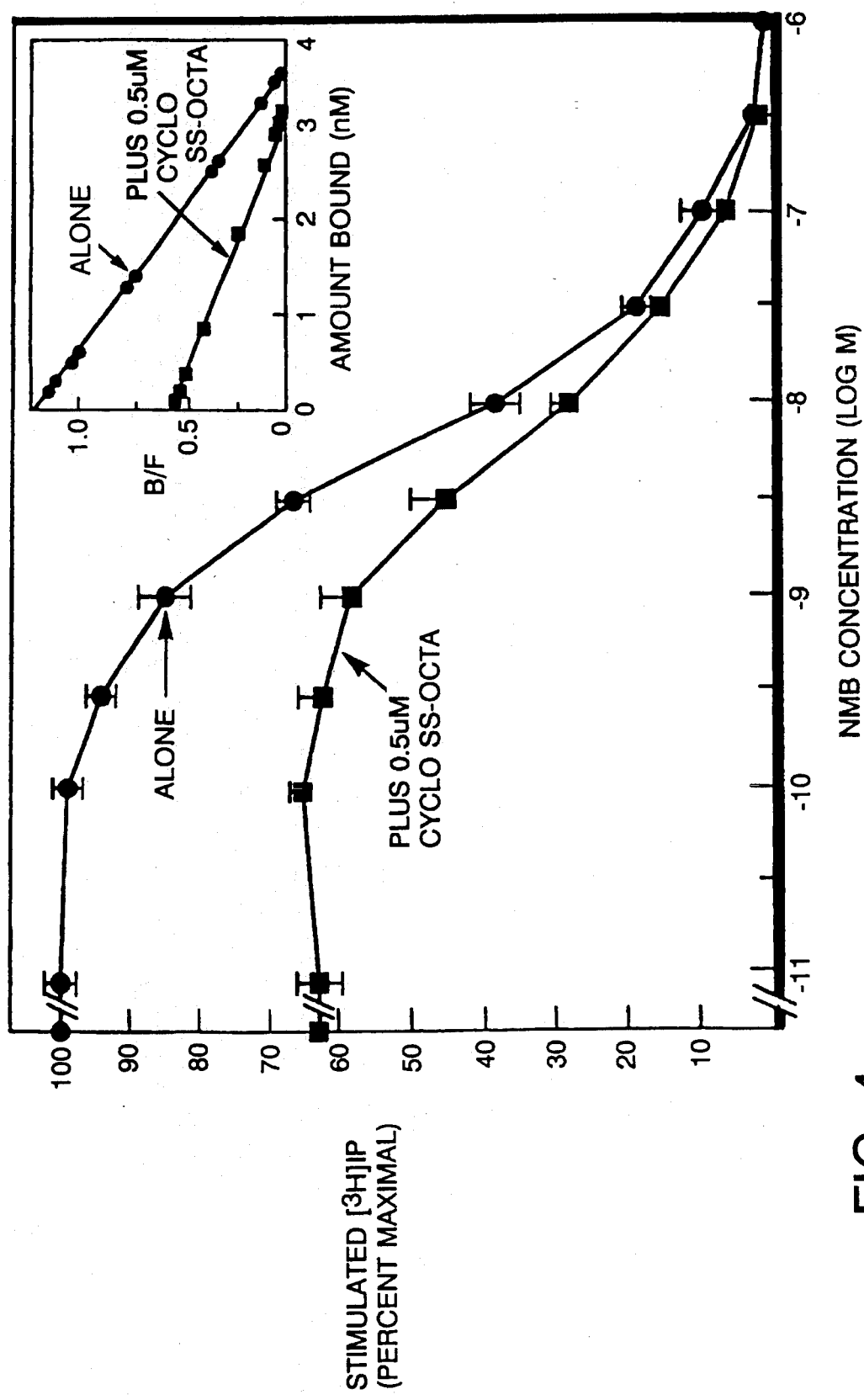
FIG. 4 is a graph showing effect of a fixed concentration of cyclo SS-octa (i.e., Analog #1) on the dose-inhibition curve of NMB for inhibiting $^{125}$I-[D-Tyr$^0$]NMB binding to NMB-R transfected cells.

To investigate further the inhibitory action of the most potent analog, cyclo SS-octa (#1; Tables 1,2), its ability to affect the dose-response curve of NMB-stimulated increases in [$^3$H]IP in NMB-R transfected cells was determined (FIG. 3) or the dose-inhibition curve of NMB for binding of $^{125}$I-[D-Tyr$^0$]NMB (FIG. 4) to these cells. The addition of 1 μM, 3 μM or 10 μM cyclo SS-octa caused a parallel rightward shift in the dose-response curve for NMB-stimulated increases in [$^3$H]IP with no change in the maximal increase if sufficiently high concentrations of NMB were used (FIG. 3). The magnitude of the rightward shift was proportional to the concentration of cyclo SS-octa and the concentration of NMB used (FIG. 3). Plotting these data in the form of Schild [Schild:H. O. Br. J. Pharmacol. 4:277 (1949)](FIG. 3, insert) gave a regression equation of y=1.1(+0.2)x+7.3 with a correlation coefficient of 0.8 (p<0.001) and the slope was not significantly different from unity. Calculation of the affinity of cyclo SS-octa for the NMB receptor from these data gave an affinity of 231±43 nM. Analysis of the ability of 0.5 μM cyclo SS-octa to affect the dose-response curve of the ability of NMB to inhibit binding of $^{125}$I-[D-Tyr$^0$]NMB to NMB-R transfected cells using a nonlinear least-squares curve fitting program [Munson, P. J. et al. Ann. Biochem. 107:220 (1980)]demonstrated that cyclo SS-octa was functioning as a competitive antagonist (FIG. 4). Specifically, 0.5 μM cyclo SS-octa caused a decrease in the affinity of NMB for NMB receptors (without cyclo SS-octa $K_d$ 3.1±0.2 and with 0.5 μM cyclo SS-octa present, $K_d$, 6.0±0.5, p<0.01). In contrast, there was no change in the total number of NMB binding sites in the presence of 0.5 μM cyclo SS-octa (without cyclo SS-octa= 7.6±0.5 pm/mg protein and with 0.5 μM cyclo SS-octa= 6.6±0.5 pm/mg protein).

To investigate the specificity of the inhibitory effects of the cyclo SS-octa analogs, the ability of a number of these analogs to inhibit binding to a number of different ligands for different receptors was determined as well as their ability to interact with NMB receptors on C-6 glioblastoma cells and alter biological responses in these cells. C-6 glioblastoma cells have been shown to possess NMB receptors [Lin, W. W. et al. J. Neurosci. 12:1077 (1992)]and therefore the ability of SS-octapeptide analogs to interact with native receptors on these cells was compared to their ability to interact with NMB receptors on NMB-R transfected cells. As demonstrated in Table 1, SS-14 and SS-28 did not inhibit binding of $^{125}$I-[D-Tyr$^0$]NMB to C-6 cells, and cyclo SS-octa was the most potent SS-octapeptide analog having an affinity of 59±9 nM. The affinities of the other 18 SS octapeptide analogs was, in general, in good agreement with that seen for the NMB receptor on NMB-R transfected cells (Table 1). The specificity of the inhibitory action of two of the most potent analogs, cyclo SS octa (#1; Table 1) and [Nal$^{6,}$Thr$^8$]-cyclo SS-octa (#2; Table 1) was demonstrated on C-6 glioblastoma cells because each of these SS-octapeptide analogs inhibited NMB-stimulated increases in [$^3$H]IP in these cells, but had no effect on endothelin-1-simulated increases in [$^3$H]IP (Table 3). Furthermore, the most potent SS-octapeptide analog, cyclo SS-octa (#1; Tables 1, 2), at 1 μM, a concentration that inhibited binding to NMB receptors on rat olfactory bulb membranes by>95%, did not inhibit binding to CCK$_A$, CCK$_B$, endothelin$_A$, PYY, bradykinin$_1$, TRH, $α_1$- or $α_2$-adrenergic, $β_1$-adrenergic, muscarinic cholinergic, benzodiazepine-neural or peripheral, dopamine$_2$, histamine H$_1$, adenosine$_1$, sigma or delta opioid, N-methyl D-aspartate receptors on plasma membranes on various tissues determined as described in METHODS.

TABLE 3

Ability of two cyclic somatostatin octapeptide analogs to inhibit NMB- and endothelin- stimulated increases in inositol phosphates in C-6 glioblastoma cells

| Peptide Added | [$^3$H]IP (dpm × 10$^3$) | | |
|---|---|---|---|
| | Alone | [Nal$^6$, Thr$^8$]-cyclo SS-octa (10 μM) | Cyclo SS-octa (10 μm) |
| None | 7.2 ± 1.0 | 7.3 ± 1.2 | 7.4 ± 1.3 |
| ET-1 (0.1 nM) | 11.0 ± 2.1 | 11.2 ± 1.9 | 10.9 ± 1.8 |
| NMB (10 nM) | 21.0 ± 1.8 | 14.3 ± 4.2* | 7.5 ± 1.0** |

Significantly different (* = p<0.05), (** = p<0.01) compared to value without SS-octapeptide analog added. C-6 glioblastoma cells (50,000 cells/well) were incubated with myo[2-$^3$H]inositol for two days, washed and then incubated with or without the indicated peptides for 60 minutes at 37° C. in phosphoinositide buffer containing 10 mM LiCl as described in METHODS. [$^3$H]IP was measured using Dowex AG1-X8 anion exchange chromatography as described in METHODS. Results are means ± SEM from three experiments and in each experiment each value was determined in duplicate.

Cyclo SS-octa did inhibit binding of [$^3$H]DAGO to mu opioid receptors on rat forebrain membranes with an affinity of 430±130 nM (Table 4) and inhibited binding of $^{125}$I-CCK-8 to CCK$_A$ receptors on rat pancreatic membranes with an affinity of 5537±7 nM. In previous studies various SS analogs have been reported to have high affinity for mu opioid receptors as well as somatostatin receptors [Maurer, R. et al. Proc. Natl. Acad. Sci. USA 79:4815 (1982); Pelton, J. T. et al. Proc. Natl. Acad. Sci. 82:236 (1985); Gulya, K., et al. Life Sci. 38:2225 (1986); and Walker, J. M. et al. Peptides 8:869 (1987)]. To compare the ability of SS-14 and SS-28 and the various SS octapeptide analogs to interact with both subtypes of Bn receptors, somatostatin and mu opioid receptors in membranes from the same species, the ability of each of these peptides to inhibit binding of $^{125}$I-[Tyr$^{11}$]SS-14 or $^{125}$I-[Tyr$^4$]Bn to cell membranes from the rat pancreatic acinar cell tumor, AR 42J cells, binding of $^{125}$I-NMB to NMB receptors on rat olfactory bulb membranes, and binding of [$^3$H]DAGO to rat forebrain membranes was determined (Table 4). Neither NMB nor GRP at concentrations up to 10 μM inhibited binding of $^{125}$I-[Tyr$^{11}$] SS-14 to somatostatin receptors on AR 42J cells or mu opioid receptors on rat forebrain membranes, and neither SS-14 nor SS-28 at concentrations up to 10 μM inhibited binding to GRP receptors on AR 42J cell membranes, NMB receptors on rat olfactory bulb membranes or mu opioid receptors on rat forebrain membranes (Table 4). There was no correlation between the affinities of the various SS-octapeptide analogs for NMB receptors on rat olfactory bulb membranes and their affinities for somatostatin receptors on AR 42J cells (r=0.1, p>0.8), their affinities for GRP receptors on rat pancreatic membranes (r=0.01, p>0.5) or their affinities for mu opioid receptors on membranes from rat forebrain (r=0.1, p>0.7) (Table 4). For example, the cyclo SS analogs cyclo SS-octa (#1; Table 1), [Nal$^{6,}$Thr$^8$]-cyclo SS-octa (#2; Table 1), [D-Phe$^1$]-cyclo SS-octa (#4; Table 1), [D-Cys$^7$]-cyclo SS-octa (#11; Table 1) and [Phe$^6$]-cyclo SS-octa varied less than 5-fold in potency for NMB receptors yet varied 800-fold for affinity for somatostatin receptors and greater than 5000-fold for mu opioid receptors (Table 4). Whereas most of the SS-octa analogs had significantly higher affinity for somatostatin receptors than NMB receptors one analog, [His⁵]-cyclo SS-octa had a 3-fold higher affinity for NMB receptors. The most potent NMB receptor antagonist cyclo SS octa (#1; Table 4) had a 10-fold greater affinity for NMB receptors than mu opioid receptors and one analog (#11; Table 4) had>50-fold higher affinity. These data demonstrate that the structural requirements of cyclo SS-octapeptide for high affinity NMB receptor occupation differ markedly from those required for high affinity somatostatin or mu opioid receptor occupation.

TABLE 4

Comparison of the affinity of NMB, GRP, SS-14, SS-28 and various SS octapeptide analogs for neuromedin B, GRP, somatostatin or mu opioid receptors on plasma membranes from AR 42J cells, rat olfactory bulb, or forebrain, respectively.

| Analog # | AR 42J Cell Membranes | | Rat Olfactory | Rat Forebrain |
|---|---|---|---|---|
| | $^{125}$I-[Tyr$^{11}$]SS-14 | $^{125}$I-[Tyr$^{4}$]Bn | $^{125}$I-NMB | [$^{3}$H]DAGO |
| NMB | >10,000 | 19 ± 1 | 1.1 ± 0.2 | >10,000 |
| GRP | >10,000 | 1.8 ± 0.1 | 297 ± 15 | >10,000 |
| SS-14 | 0.13 ± 0.01 | >50,000 | >40,000 | >10,000 |
| SS-28 | 0.40 ± 0.20 | >10,000 | >10,000 | >10,000 |
| 1 | 0.80 ± 0.50 | 2870 ± 520 | 43 ± 9 | 430 ± 130 |
| 2 | 0.50 ± 0.10 | 950 ± 70 | 85 ± 20 | 1.9 ± 0.7 |
| 4 | 0.24 ± 0.13 | 2000 ± 150 | 245 ± 130 | 650 ± 130 |
| 5 | 0.29 ± 0.03 | 3900 ± 1200 | 800 ± 200 | 2.0 ± 1.4 |
| 7 | 0.86 ± 0.23 | 750 ± 10 | 740 ± 160 | 200 |
| 8 | 3.9 ± 0.1 | 4100 ± 750 | 1480 ± 500 | 280 |
| 9 | 2.8 ± 0.7 | 1540 ± 180 | 590 ± 170 | 1160 |
| 10 | 91 ± 23 | 1500 ± 160 | 920 ± 350 | 1020 |
| 11 | 48 ± 3 | 7620 ± 1260 | 230 ± 70 | >10,000 |
| 12 | 3.1 ± 1.6 | 2100 ± 150 | 1180 ± 520 | >10,000 |
| 13 | 194 ± 27 | 2150 ± 200 | 270 ± 90 | 1640 |
| 14 | 1870 ± 30 | 3100 ± 700 | 470 ± 240 | 500 |
| 17 | 570 ± 180 | 3710 ± 200 | 850 ± 300 | 1570 |

Membranes prepared from rat olfactory bulb, rat forebrain or AR 42J cells as described in METHODS were incubated with the indicated ligands as described in METHODS. Affinities were calculated by the method of Cheng, Y.C. et al. Biochem. Pharmacol. 22:2099 (1973). Results are means ± 1SEM from at least three experiments.

Further evidence that the various cyclo SS-octapeptide analogs were not altering NMB receptor affinity by occupying SS receptors was that no saturable binding of $^{125}$I [Tyr$^{11}$]SS-14 was detected to glioblastoma C-6 cells or the NMB-R transfected cells (n=3). The $^{125}$I-[Tyr$^{11}$]SS-14 used bound to dispersed guinea pig pancreatic acini, which has been shown to possess high affinity SS receptors [Esteve, J. P. et al. Am. J. Physiol 247:G62 (1984)].

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of selectively inhibiting inositol phosphate production in cells induced by neuromedin B, said method comprising the step of contacting said cells with an octapeptide of the formula:

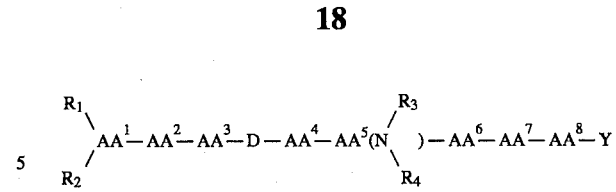

wherein $AA^1$ is the D- or L-isomer of an aromatic α-amino acid;
$AA^2$ is the D- or L-isomer of Cys;
$AA^3$ is F₅Phe, Phe, or X-Phe in which X is OH;
$AA^4$ is Trp or an aromatic α-amino acid;
$AA^5$ is Lys or Orn;
$AA^6$ is Leu, Ile, Nle, Val, Nal, or Phe;
$AA^7$ is the D- or L-isomer of Cys;
$AA^8$ is the D- or L-isomer selected from the group consisting of an aromatic α-amino acid, Thr and Ser;
each $R_1$ and $R_2$, independently, is H, $C_{1-12}$ alkyl, $C_{2-12}$ alkenyl, $C_{2-12}$ alkynyl, phenyl, naphthyl, $C_{7-12}$ phenylalkyl, $C_{8-12}$ phenylalkenyl, $C_{8-12}$ phenylalkynyl, $C_{11-20}$ naphthylalkyl, $C_{12-20}$ naphthylalkenyl, $C_{12-20}$ naphthylalkynyl, COE, or COOE in which E is $C_{1-12}$ alkyl, $C_{2-12}$ alkenyl, $C_{2-12}$ alkynyl, phenyl, naphthyl, $C_{7-12}$ phenylalkyl, $C_{8-12}$ phenylalkenyl, $C_{8-12}$ phenylalkynyl, $C_{11-20}$ naphthylalkyl, $C_{12-20}$ naphthylalkenyl, or $C_{12-20}$ naphthylalkynyl, provided that when one of $R_1$ or $R_2$ is COE or COOE, the other must be H;
each $R_3$ and $R_4$, independently, is H, $C_{1-12}$ alkyl, $C_{2-12}$ alkenyl, $C_{2-12}$ alkynyl, phenyl, naphthyl, $C_{7-12}$ phenylalkyl, $C_{8-12}$ phenylalkenyl, $C_{8-12}$ phenylalkynyl, $C_{11-20}$ naphthylalkyl, $C_{12-20}$ naphthylalkenyl, or $C_{12-20}$ naphthylalkynyl; and
Y is $OR_5$ or $NR_6R_7$ in which each $R_5$, $R_6$ and $R_7$, independently, is H, $C_{1-12}$ alkyl, $C_{2-12}$ alkenyl, $C_{2-12}$ alkynyl, phenyl, naphthyl, $C_{7-12}$ phenylalkyl, $C_{8-12}$ phenylalkenyl, $C_{8-12}$ phenylalkynyl, $C_{11-20}$ naphthylalkyl, $C_{12-20}$ naphthylalkenyl, or $C_{12-20}$ naphthylalkynyl;
provided that AA¹ and AA² cannot both be D-isomers; and further provided that if AA⁸ is Thr or Ser, AA⁶ cannot be Val.

2. The method of claim 1, wherein AA³ is Tyr.
3. The method of claim 1, wherein AA⁴ is Trp or Nal.
4. The method of claim 2, wherein AA⁴ is Trp or Nal.
5. The method of claim 1, wherein each $R_3$ and $R_4$, independently, is H.
6. The method of claim 4, wherein each $R_3$ and $R_4$, independently, is H.
7. The method of claim 1, wherein AA⁵ is Lys.
8. The method of claim 1, wherein AA⁶ is Val.
9. The method of claim 1, wherein AA⁶ is Nal.
10. The method of claim 1, wherein AA⁸ is Thr.
11. The method of claim 1, wherein AA⁸ is an aromatic α-amino acid.
12. The method of claim 1, wherein AA¹ is a D-isomer and AA⁸ is an L-isomer, or AA¹ is a L-isomer and AA⁸ is an D-isomer.
13. The method of claim 1, wherein said octapeptide is of the formula:

H₂-D-Nal-Cys-Tyr-D-Trp-Lys-Val-Cys-Nal-NH₂;
H₂-D-Nal-Cys-Tyr-D-Trp-Lys-Nal-Cys-Thr-NH₂;
H₂-D-Nal-Cys-Tyr-D-Trp-Lys-Nal-Cys-Nal-NH₂;
H₂-D-Phe-Cys-Tyr-D-Trp-Lys-Val-Cys-Nal-NH₂;
H₂-D-Nal-Cys-Tyr-D-Trp-Lys-Val-Cys-D-Nal-NH₂;
H₂-Nal-Cys-Tyr-D-Trp-Lys-Val-Cys-D-Nal-NH₂;
H₂-D-Nal-D-Cys-Tyr-D-Trp-Lys-Val-Cys-Nal-NH₂;
H₂-D-Nal-Cys-Tyr-D-Trp-Lys-Val-D-Cys-Nal-NH₂;
H₂-D-Trp-Cys-Tyr-D-Trp-Lys-Val-Cys-Nal-NH₂;
H₂-D-Nal-Cys-Tyr-D-Trp-Lys-Phe-Cys-Nal-NH₂;
H₂-D-Nal-Cys-Tyr-D-Nal-Lys-Val-Cys-Nal-NH₂;
H₂-D-phe-Cys-Tyr-D-Trp-Lys-Nal-Cys-Thr-NH₂; or
H₂-D-Nal-Cys-Tyr-D-Trp-Orn-Val-Cys-Nal-NH₂.

14. A method of selectively inhibiting inositol phosphate production in cells induced by neuromedin B, said method comprising the step of contacting said cells with an octapeptide of the formula:

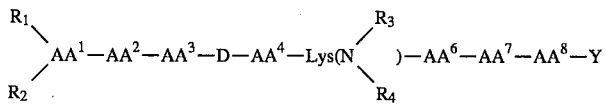

wherein
AA¹ is the D- or L-isomer of an aromatic α-amino acid;
AA² is the D- or L-isomer of Cys;
AA³ is F₅Phe, Phe, or X-Phe in which X is OH;
AA⁴ is Trp or an aromatic α-amino acid;
AA⁶ is Thr or Ser;
AA⁷ is the D- or L-isomer of Cys;
AA⁸ is the D- or L-isomer selected from the group consisting of an aromatic α-amino acid;
each $R_1$ and $R_2$, independently, is H, $C_{1-12}$ alkyl, $C_{2-12}$ alkenyl, $C_{2-12}$ alkynyl, phenyl, naphthyl, $C_{7-12}$ phenylalkyl, $C_{8-12}$ phenylalkenyl, $C_{8-12}$ phenylalkynyl, $C_{11-20}$ naphthylalkyl, $C_{12-20}$ naphthylalkenyl, $C_{12-20}$ naphthylalkynyl, COE, or COOE in which E is $C_{1-12}$ alkyl, $C_{2-12}$ alkenyl, $C_{2-12}$ alkynyl, phenyl, naphthyl, $C_{7-12}$ phenylalkyl, $C_{8-12}$ phenylalkenyl, $C_{8-12}$ phenylalkynyl, $C_{11-20}$ naphthylalkyl, $C_{12-20}$ naphthylalkenyl, or $C_{12-20}$ naphthylalkynyl, provided that when one of $R_1$ or $R_2$ is COE or COOE, the other must be H;

each $R_3$ and $R_4$, independently, is H, $C_{1-12}$ alkyl, $C_{2-12}$ alkenyl, $C_{2-12}$ alkynyl, phenyl, naphthyl, $C_{7-12}$ phenylalkyl, $C_{8-12}$ phenylalkenyl, $C_{8-12}$ phenylalkynyl, $C_{11-20}$ naphthylalkyl, $C_{12-20}$ naphthylalkenyl, or $C_{12-20}$ naphthylalkynyl; and Y is $OR_5$ or $NR_6R_7$ in which each $R_5$, $R_6$ and $R_7$, independently, is H, $C_{1-12}$ alkyl, $C_{2-12}$ alkenyl, $C_{2-12}$ alkynyl, phenyl, naphthyl, $C_{7-12}$ phenylalkyl, $C_{8-12}$ phenylalkenyl, $C_{8-12}$ phenylalkynyl, $C_{11-20}$ naphthylalkyl, $C_{12-20}$ naphthylalkenyl, or $C_{12-20}$ naphthylalkynyl; provided that AA¹ and AA² cannot both be D-isomers.

15. The method of claim 14, wherein AA¹ is D-Phe.
16. The method of claim 14, wherein AA³ is Tyr.
17. The method of claim 14, wherein AA⁴ is Trp.
18. The method of claim 15, wherein AA³ is Tyr.
19. The method of claim 15, wherein AA⁴ is Trp.
20. The method of claim 19, wherein AA³ is Tyr.
21. The method of claim 14, wherein AA⁵ is Lys.
22. The method of claim 14, wherein AA⁶ is Thr.
23. The method of claim 14, wherein AA¹ is a D-isomer and AA⁸ is an L-isomer, or AA¹ is a L-isomer and AA⁸ is an D-isomer.
24. The method of claim 14, wherein said octapeptide is of the formula:

H₂-D-Phe-Cys-Tyr-D-Trp-Lys-Thr-Cys-Nal-NH₂;
H₂-D-Phe-Cys-Tyr-D-Trp-Lys(iPr)-Thr-Cys-Nal-NH₂;
H₂-D-Phe-Cys-Tyr-D-Trp-Lys(diEt)-Thr-Cys-Nal-NH₂
H₂-D-Phe-Cys-Tyr-D-Trp-Lys-Ser-Cys-Thr-NH₂;
H₂-D-Nal-Cys-Tyr-D-Trp-Lys-Thr-Cys-Nal-NH₂;
H₂-D-Nal-D-Cys-Tyr-D-Trp-Lys-Thr-Cys-Nal-NH₂; or
H₂-D-Nal-Cys-Phe-D-Trp-Lys-Thr-Cys-Nal-NH₂.

* * * * *

UNITED STATES PATENT AND TRADEMARK OFFICE
CERTIFICATE OF CORRECTION

PATENT NO.   : 5,462,926

DATED        : October 31, 1995

INVENTOR(S)  : David H. Coy and John E. Taylor

It is certified that error appears in the above-identified patent and that said Letters Patent is hereby corrected as shown below:

Column 9, line 66, replace "$\alpha_1$-adrenergic, $\alpha_2$-adrenergic," with --$\alpha_1$-adrenergic, $\alpha_2$-adrenergic,--;

Column 10, line 46, replace "Jo 286:641" with --J. 286:641--;

Column 13, Table 2, line 36, last line of footnote, replace "experiment, each value was determin" with --experiment, each value was determined in duplicate--.

Signed and Sealed this

Twentieth Day of February, 1996

Attest:

BRUCE LEHMAN

Attesting Officer

Commissioner of Patents and Trademarks